United States Patent [19]

Itoh et al.

[11] Patent Number: 5,279,744

[45] Date of Patent: Jan. 18, 1994

[54] METHOD FOR PURIFICATION OF AN AMINO ACID USING ION EXCHANGE RESIN

[75] Inventors: Hisao Itoh, Saga; Katsumi Toide; Masao Ikeda, both of Kawasaki, all of Japan

[73] Assignee: Ajinomoto Co., Inc., Tokyo, Japan

[21] Appl. No.: 764,450

[22] Filed: Sep. 24, 1991

[30] Foreign Application Priority Data

Sep. 25, 1990 [JP] Japan .................. 2-254707

[51] Int. Cl.⁵ .................. B01D 15/02; B01D 15/04
[52] U.S. Cl. .................. 210/676; 210/692; 562/554; 562/562; 562/573
[58] Field of Search ............... 210/670, 672, 676, 685, 210/692; 548/344; 562/554, 562, 573

[56] References Cited

U.S. PATENT DOCUMENTS 3,445,382  5/1969  Frederick .
3,573,004  3/1971  Abrams et al. .
4,714,767  12/1987  Tanaka et al. .................. 548/344
5,000,794  3/1991  Kulprathipanja .................. 210/660

FOREIGN PATENT DOCUMENTS 1303056  6/1971  Fed. Rep. of Germany .
1591950  6/1970  France .

OTHER PUBLICATIONS

Greenstein et al., Chemistry of the Amino Acids, vol. 2, John Wiley & Sons, Inc. (NY) pp. 1452–1461.

Primary Examiner—Ivars Cintins
Attorney, Agent, or Firm—Oblon, Spivak, McClelland, Maier & Neustadt

[57] ABSTRACT

A method for purification of an amino acid which comprises contacting an amino acid solution containing impurities with an ion exchange resin to selectively adsorb the amino acid onto the resin, eluting and recovering the adsorbed amino acid whereby the resin is contacted with the amino acid solution in countercurrent continuous multiple steps during adsorption and an eluent is contacted with the adsorbed resin in countercurrent continuous multiple steps during elution.

4 Claims, 2 Drawing Sheets

METHOD FOR PURIFICATION OF AN AMINO ACID USING ION EXCHANGE RESIN

BACKGROUND OF THE INVENTION

1. Field of the Invention:

The present invention relates to a method for purification of an amino acid using ion exchange resin, whereby the amino acid is contacted with the resin in countercurrent continuous multiple steps to greatly reduce the required amount of resin and the amount of water necessary for washing the resin.

2. Discussion of the Background:

Ion exchange resins have been widely used in purification and collection of highly pure amino acids from crude amino acid solutions industrially prepared by fermentation, synthesis and extraction. Serious problems involved in the use of ion exchange resin are that they require large amounts of resin and use large amounts of water. That is, where an amino acid is purified, it has been heretofore conventional to apply fixed bed operations using ion exchange resin. This technique comprises an adsorption step in which a fermentation broth of an amino acid having a pH adjusted to a specific value is contacted with a salt type, strongly acidic cation exchange resin layer, such as an ammonia type, etc. to adsorb the amino acid onto the resin layer. This step is followed by an elution step in which the amino acid is eluted with an eluent such as ammonia water, and the ion exchange resin is regenerated to a salt type.

When fermentation broth is passed through a conventional resin tower in the adsorption step, washing water is passed through after the fermentation broth in order to permit the fermentation broth to completely pass through the resin layer. In the elution step, washing water is passed after the fermentation broth in order to permit an eluent to completely pass through the resin layer. Furthermore, suspended substances in the fermentation broth are deposited in the resin tower during the adsorption step so that large amounts of washing water flowing in the reverse direction are needed to remove the deposit after completion of adsorption. This is not the only reason that water needs increase. The amount of water discharged during elution is large and facilities for treatment of the waste water become huge.

The amount of washing water increases as the amount of resin used increases. It is thus expected that by reducing the amount of resin used, the amount of washing water can be reduced and hence, facilities required for resin operations can be down-sized. Based on this expectation, various methods for reducing the amount of washing water used have been investigated (Japanese Patent Application Laid-open Nos. 50-127879, 52-11173 and 62-65690) but a considerable amount of washing water is still required.

SUMMARY OF THE INVENTION

An object of the present invention is to provide a method for greatly reducing the amount of water used for washing an ion exchange resin and therefore reducing waste water and greatly improving productivity of the resin, in a method for purification of an amino acid using ion exchange resin.

DETAILED DESCRIPTION OF THE PREFERRED EMBODIMENTS

The present inventor has made investigations on the ion exchange resin step in purification of amino acids using ion exchange resins and has discovered a method for greatly improving the productivity of the resin and greatly reducing the amount of water used for washing out suspended substances adhered and deposited on the resin layer. That is, the present invention provides a method free of the foregoing problems and is characterized by contacting an amino acid solution containing impurities with ion exchange resin in countercurrent continuous multiple steps and contacting an eluent with the adsorbed resin in countercurrent continuous multiple steps, whereby purification of the amino acid containing impurities can be made using a small amount of the resin and a small amount of washing water.

The amino acid solution to which the present invention can be applied is an amino acid solution containing impurities industrially prepared by fermentation, synthesis or extraction. These amino acid solutions include a wide variety of solutions, for example, a fermentation broth itself of an amino acid such as lysine or glutamic acid, a solution obtained by removing solid impurities such as fermentation cells from a fermentation broth and mother liquor of crystallization which remains after isolating and collecting the desired amino acid from the fermentation broth by known methods such as pH controlled crystallization (isoelectric point crystallization).

The ion exchange resin which is contacted with the amino acid solution may be any cation exchange resin or anion exchange resin, but a strongly acidic cation exchange resin is generally used. The resin may be any free type, but in general, a salt type is used. Such cation exchange resins may be of gel type or macroporous type; "DIAION SK-1B" manufactured by Mitsubishi Chemical Industry Co., Ltd. is an example of the former and "AMBERLITE 200C" manufactured by Rohm & Haas Co., Ltd. is an example of the latter. In practicing the method of the present invention, selection and determination of the ion exchange resin which may be anion or cation, gel type or macroporous type, free type or salt type may be easily made by one skilled in the art based on simple experiments to determine adsorption and elution behavior.

Figure 1:
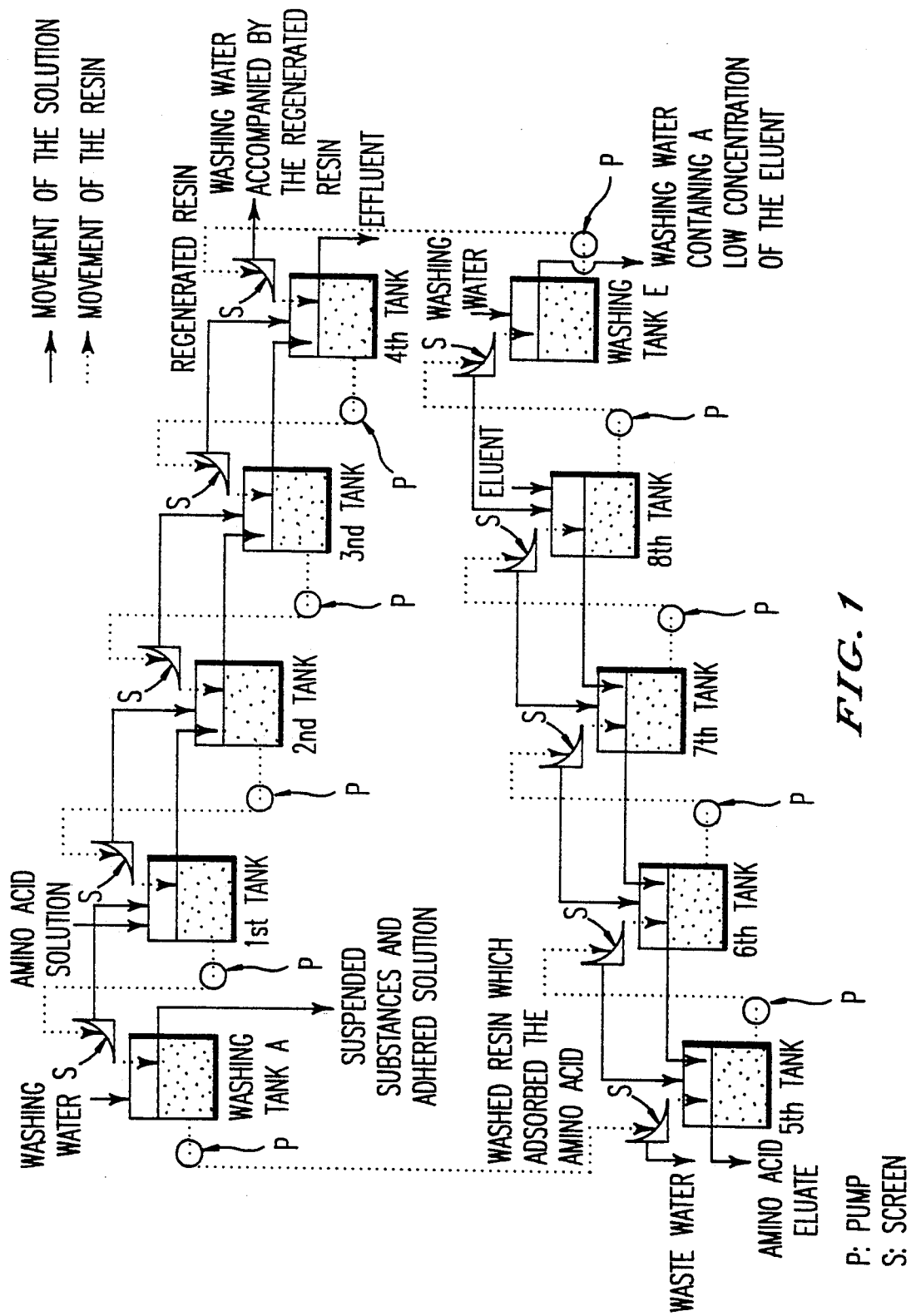
FIG. 1 is a flow chart of an embodiment of the method of the present invention.
Figure 2A:
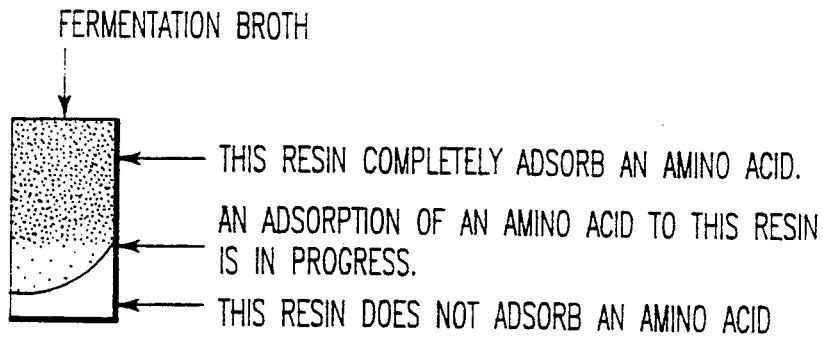
FIGS. 2a–2c illustrate problems in conventional resin operations.
Figure 2B:
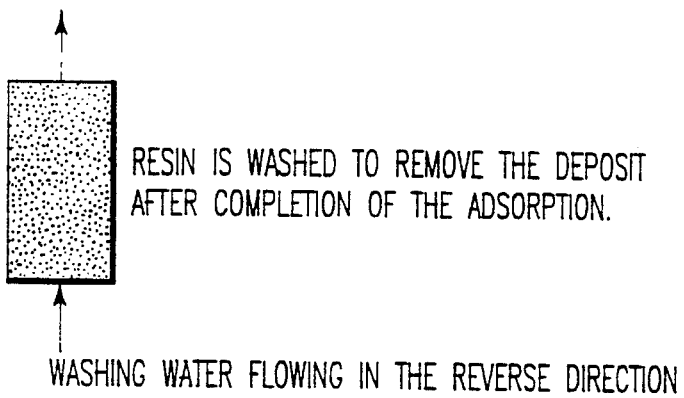
Figure 2C:
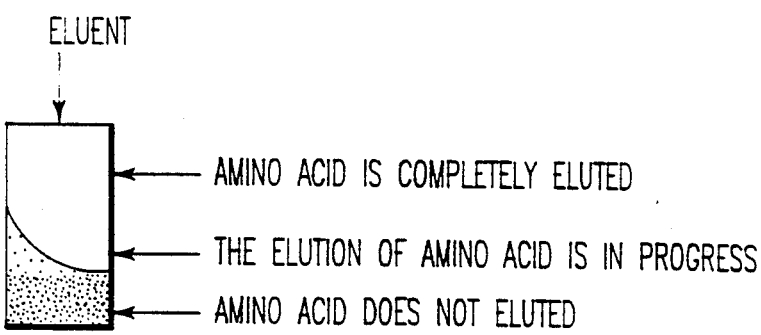

An embodiment of the method according to the present invention is illustratively shown in FIG. 1 but as long as the countercurrent continuous multiple steps can be achieved, the present invention is not limited to this embodiment. The figure illustrates the embodiment composed of 4 steps each for adsorption, 4 steps for elution and one step each for the washing step. However, the number of steps is determined according to the degree of reduction of amino acid concentration in the effluent. The number of steps in the elution step is determined by the amino acid concentration in the eluent and yield of the elution. In the figure, movement of the solution is shown by solid line and movement of the resin is shown by dotted line. The movement of the solution is made, for example, by overflow and the movement of the resin is made, for example, using pump (P).

The amino acid solution containing impurities is fed to a first tank and then to a second tank, a third tank and a fourth tank, in order, during which the amino acid is adsorbed to the resin of each tank. The solution is withdrawn from the fourth tank as an effluent. On the other hand, the regenerated resin is supplied from washing tank E to the fourth tank and goes to the first tank via the third and second tanks, while countercurrently contacting the amino acid solution. In order to remove the solution accompanied by the resin in this case, an apparatus for separating the resin and the solution from each other, such as screen (S) between the respective tanks is provided to improve efficiency. The resin to which the amino acid has thus been adsorbed is withdrawn from the first tank and sent to the washing step in washing tank A to wash off suspended substances adhered to the resin and the adhered solution.

Washing is accomplished by showering or washing in a stirring tank, but the washing method is determined depending on concentration of the suspended substances in the eluent. Also in order to prevent intake of impurities into the elution step, the adhered impurities are reduced to as low a level as possible by countercurrent two step washing or centrifugal dehydration.

The washed resin is sent to a fifth tank in the elution step. In the elution step, the resin is sent from the fifth tank to a sixth tank, a seventh tank and then an eighth tank, in order, while eluting the adsorbed amino acid from the fifth tank. On the other hand, the eluent is supplied to the eighth tank and sent to reach the fifth tank, while countercurrently contacting with the resin. From the fifth tank, the solution is withdrawn out of the system as an amino acid eluent and then sent to the next step of recovering the amino acid. After the resin is out of the eighth tank, the resin is sent to the washing step in washing tank E to wash off the adhered eluent and then recycled from the fourth tank to the adsorption step and reused there as the regenerated resin.

The washing water containing a low concentration of the eluent or the washing water which is accompanied by the regenerated resin supplied from washing tank E to the fourth tank and separated by a screen, etc. may be used for preparation of the eluent. That is, the washing water is utilized as diluting water for preparing the eluent by diluting conc. sulfuric acid, conc. ammonia water, etc. or as dissolving water for preparing the eluent by dissolving sodium carbonate, etc. in water. By doing so, environmental pollution by the eluent source via discharge of washing water is prevented and the source of eluent is also saved.

Ion exchange in each tank may be accelerated by thoroughly mixing the solution and the resin with stirring the contents in each tank.

The term "continuous" as used in the method of the present invention includes not only completely literal continuous operation but also continual operation in a part of or the whole of the steps. In more detail, the completely continuous operation refers to one where the amino acid solution and the eluent are continuously supplied to the system and continuously withdrawn out of the system as the effluent and the eluate, during which washing is performed continuously in the washing tanks to allow the resin to continuously move between the respective tanks. An example of the continual operation is that the amino acid and/or the eluent is intermittently supplied to the system in the adsorption step and/or the elution step and the resin in each tank is moved altogether during which the supply is discontinued.

In order to recover the amino acid from the amino acid solution obtained by the method of the present invention as described above, conventionally known techniques for recovery such as crystallization by concentration and isoelectric point crystallization may be used.

In conventional ion exchange resin operations of fixed bed type, the resin is often ineffectively used in one tower for all of adsorption step (a) washing step (b) and elution step (c). In order to effectively use the resin, it is necessary to make some device like increasing the number of towers. However, this change results in complicated facilities so that fixed costs increase. Further according to conventional methods, back washing is performed to remove suspended substances but the resin does not function as a resin during the washing. In this case, large amounts of water are used so that the amount of water discharged becomes large. As the result, facilities for treating waste water must be of large scale. As stated above, the conventional operations involve many problems in view of productivity of resin and the amount of waste water.

On the contrary, according to the method of the present invention, the saturated resin in the amino acid solution is instantaneously sent to the elution step. Therefore, the resin always exhibits its inherent function of performing ion exchange so that productivity of the resin is high. In addition, no back washing is necessary so that the total amount of water used is smaller and the amount of waste water can be reduced. Thus the objects of the present invention have been attained.

Other features of the invention will become apparent in the course of the following descriptions of exemplary embodiments which are given for illustration of the invention and are not intended to be limiting thereof.

EXAMPLE 1

(1) Sulfuric acid was added to a fermentation broth (pH 7.0) of lysine (Lys) obtained using beet molasses as a raw material to adjust the pH to 2.0. The lysine concentration in this case was 7.4 g/dl. As an ion exchange resin for adsorption, strongly acidic cation exchange resin "DIAION SK-1B" of ammonia type was used in an amount of 1 liter per each tank.

As shown in FIG. 1, the pH-adjusted lysine fermentation broth (sample solution) was supplied to a first tank in a flow amount of 6 liters/hr. The resin for adsorption (regenerated resin after it reached the stationary state) was supplied to a fourth tank in a flow amount of 6 liters/hr. On the other hand, 3N ammonia water was used as an eluent and supplied to an eighth tank in a flow amount of 6 liters/hr. With respect to washing water, 5.5 liters/hr of washing water was supplied to wash the resin transferred from the first tank to washing tank A. In order to remove adhered ammonia water from the elution-completed resin transferred from the eighth tank to washing tank E, 4.5 liters/hr of washing water was supplied. The washing water containing ammonia can be used for diluting conc. ammonia water in preparing the eluent by diluting conc. ammonia water.

The eluent containing lysine was recovered from a fifth tank and the effluent was discharged from the fourth tank these operations were completely continuous.

(2) Next, for purpose of comparison, the same lysine fermentation broth was treated by conventional resin operation of fixed bed type. The conventional operation is described in Japanese Patent Application Laid-open No. 61-24548. That is, as in (1) above, the following resin operations were performed by 3-tower-adsorption-3-tower-elution method, using 5 towers packed with 1 liter of strongly acidic cation exchange resin "DIAION SK-1B" of ammonia type.

| | |
|---|---|
| adsorption | SV = 1.8 |
| displacement | SV = 1.8 |
| countercurrent washing | SV = 2.2 |
| elution | SV = 0.96 |
| displacement | SV = 1.8 |

(3) The results are shown in Table 1. The results of the method according to the present invention are those obtained in the stationary state, of course.

TABLE 1

| | This Invention | Conventional Method |
|---|---|---|
| Concentration of eluted Lys | 12 g/dl | 12 g/dl |
| Rate of discharged washing water to sample solution | 80% | 350% |
| Amount of washing water used | 1 | 4.4 |
| Recovery rate of Lys | 96% | 99% |
| Productivity of resin | 3 or more | 1 |

As is understood from Table 1, according to the present invention the yield of lysine somewhat decreases but the concentration of the eluent is the same as the conventional method, so that the amount of waste water is greatly reduced. It is thus unnecessary to subject the waste water to treatment with activated sludge process so that costs for treating the waste water, and facility costs can be reduced. In addition, the amount of the treatment per the resin becomes about 3 times that of the conventional method so that costs for resin operations can also be reduced.

EXAMPLE 2

(1) Mother liquor for crystallization (pH 3.2, glutamic acid concentration of 1.92 g/dl) was obtained from a fermentation broth of glutamic acid (Glu) by isolating glutamic acid through isoelectric point crystallization. To the mother liquor was added 96% sulfuric acid to reduce the pH to 1.5. The thus obtained solution was used as a sample solution.

The solution was contacted with the resin in a manner similar to Example 1, except that "DIAION PK-212L" (cation exchange resin manufactured by Mitsubishi Chemical Industry Co., Ltd.) of $NH_4$ type was used and a solution obtained by adding 1% sodium carbonate to a glutamic acid fermentation broth (glutamic acid concentration of 8.5 g/dl) was used as the eluent. Flow amounts in the respective parts were the same as in Example 1.

(2) Comparison with a conventional method was also made in a manner similar to Example 1.

(3) The results are collectively shown in Table 2.

TABLE 2

| | This invention | Conventional Method |
|---|---|---|
| Concentration of eluted Glu | 6.9 g/dl | 6.9 g/dl |
| Rate of discharged washing water to sample solution | 190% | 460% |
| Amount of washing water used | 1 | 2.4 |
| Recovery rate of Glu | 83% | 87% |
| Productivity of resin | 3 or more | 1 |

Also in this example, decrease in the yield was noted as in Example 1 but it was possible to greatly reduce the amount of water used and the amount of waste. It was also possible to greatly improve the productivity of the resin.

What is claimed as new and desired to be secured by Letters Patent of the United States is:

1. A method for purification of an amino acid which comprises: contacting a lysine or glutamic acid solution containing impurities with an ion exchange resin contained in a plurality of tanks to selectively adsorb said lysine or glutamic acid onto the resin, eluting and recovering the adsorbed amino acid, wherein the resin is contacted with the amino acid solution while moving the resin from tank to tank in countercurrent continuous multiple steps during adsorption and an eluent is contacted with the adsorbed resin in countercurrent continuous multiple steps during elution.

2. The method of claim 1 wherein said ion exchange resin is a strongly acidic cation exchange resin.

3. The method of claim 1 wherein said amino acid is lysine.

4. The method of claim 1 wherein said amino acid is glutamic acid.

* * * * *